United States Patent [19]

Schwindeman

[11] Patent Number: 5,403,946
[45] Date of Patent: Apr. 4, 1995

[54] PROCESS OF PREPARING TRIMETHYLSILYLOXY FUNCTIONALIZED ALKYLLITHIUM COMPOUNDS

[75] Inventor: James A. Schwindeman, Charlotte, N.C.

[73] Assignee: FMC Corporation, Philadelphia, Pa.

[21] Appl. No.: 279,721

[22] Filed: Jul. 25, 1994

[51] Int. Cl.$^6$ ............................ C07F 7/08; C07F 7/18
[52] U.S. Cl. .................... 556/466; 556/482; 556/486
[58] Field of Search ........................ 556/466, 482, 486

[56] References Cited

U.S. PATENT DOCUMENTS

| | | | |
|---|---|---|---|
| 3,511,865 | 5/1970 | Peterson | 556/466 |
| 5,082,961 | 1/1992 | Fukumoto et al. | 556/466 |
| 5,231,205 | 7/1993 | Rieke | 556/466 X |
| 5,321,148 | 6/1994 | Schwindeman | 556/466 |

Primary Examiner—Paul F. Shaver
Attorney, Agent, or Firm—Charles C. Fellows; Robert L. Andersen

[57] ABSTRACT

A process for producing compounds of the formula $(CH_3)_3SiORLi$ where in R is selected from alkyl groups containing 2 to 10 carbon atoms and aryl groups containing 6 to 10 carbon atoms by reacting, in an inert atmosphere, in a hydrocarbon solvent, a haloalcohol of the formula HORX wherein R is selected from alkyl groups containing 2 to 10 carbon atoms and aryl groups containing 6 to 10 carbon atoms and X is selected from chlorine or bromine, is reacted with hexamethyldisilazane at a temperature between 20° C. and the reflux temmperature of the solvent after which the resulting product, a trimethylsilyloxyalkylhalide compound, is reacted at a temperature between 50° and 160° C., with powdered lithium metal to produce the $(CH_3)_3SiORLi$ compound.

7 Claims, No Drawings

PROCESS OF PREPARING TRIMETHYLSILYLOXY FUNCTIONALIZED ALKYLLITHIUM COMPOUNDS

The present invention concerns an improved process for preparing functionalized alkyllithium compounds of the formula $(CH_3)_3SiORLi$.

Functionalized organolithium compounds have been used in organic synthesis reactions for some time and more recently have been used as initiators in the anionic polymerization of olefinic monomers. United Kingdom published patent application 2,241,239 discloses producing initiators of the formula $R^1 R^2R^3SiOALi$ wherein $R^1$, $R^2$ and $R^3$ are aliphatic and aromatic radicals and A is a hydrocarbon bridging group. This patent recommended using a 1.5 to 6 stoichiometric excess of lithium, an excess of 6 was used in the examples, to get high yields. Reaction temperatures below 50° C. were employed because above 40° C. undesired by-products were observed.

U.S. Pat. No. 5,321,148, issued Jun. 14, 1994 discloses a process for preparing functionalized alkyllithium compounds by reacting a fine particle size lithium metal of not more than 300 microns average particle size with an organosiloxyalkyl halide of the formula $R^1R^2R^3SiORX$ wherein $R^1$, $R^2$ and $R^3$ are independently selected from alkyl groups containing 1 to 10 carbon atoms and aryl groups containing 6 to 10 carbon atoms, R is selected from alkyl groups containing 1 to 8 carbon atoms either straight chain or substituted by alkyl or aryl groups, X is selected from chlorine or bromine, the reaction temperature is above 50° C., the reaction medium is a hydrocarbon solvent and the reaction is conducted in an inert atmosphere. Compounds of the formula $R^1R^2R^3SiORX$, when $R^1$, $R^2$ and $R^3$ are methyl, prepared according to the disclosed process (Comparative Example C-1 herein), have been found to not uniformly lithiate requiring more halide feed and resulting in slow filtration rates and lower than expected yields. The lithiation reaction is exothermic so over feeding the halide to overcome the lack of lithiation initiation could easily result in uncontrolable and dangerous exotherm in large or plant scale reactions.

The present invention provides a process for producing compounds of the formula $(CH_3)_3SiORLi$ where in R is selected from alkyl groups containing 2 to 10 carbon atoms and aryl groups containing 6 to 10 carbon atoms by reacting a haloalcohol of the formula HORX, wherein R has the meaning ascribed above and X is chlorine or bromine, in a hydrocarbon solvent, with hexamethyldisilazane after which the resulting product, a trimethylsilyloxyalkylhalide compound, is reacted with powdered lithium metal to produce the desired trimethylsilyloxyalkyllithium compound. The first step of the reaction can be done at temperatures from room temperature, about 20° C., to the reflux temperature of the solvent; the second step of the reaction is done at a temperature that is between 50° and 160° C., with the reflux temperature of the solvent being preferred. Both the first and second step of the process are conducted in an inert atmosphere.

The haloalcohol is of the formula HORX, wherein R is selected from alkyl groups of 2 to 10 carbon atoms, straight chain or substituted by alkyl or aryl groups and aryl groups containing 6 to 10 carbon atoms and X is chloro or bromo. The trimethylsilyloxyalkylhalide compounds are produced in hydrocarbon solution by reaction of the haloalcohol with the hexamethyldisilylazane. The reaction can be catalyzed by a number of catalysts, for example trimethylsilyl chloride. Trimethylsilyloxyalkylhalides useful in the practice of this invention include but are not limited to 6-(trimethylsilyloxy)-1-hexylhalide, 3-(trimethylsilyloxy)-2,2-dimethyl-1-propylhalide, 3-(trimethylsilyloxy)-1-propylhalide, 4-(trimethylsilyloxy)-1-butylhalide, 3-(trimethylsilyloxy)-2-methyl-1-propylhalide, 8-(trimethylsilyloxy)-1-octylhalide, and the like.

The reaction solvent is a non-polar hydrocarbon solvent selected from aliphatic, cycloaliphatic and aromatic hydrocarbons or mixtures thereof. Preferred solvents are aliphatic, cycloaliphatic and aromatic hydrocarbons, especially alkanes having 3 to 12 carbon atoms, cycloalkanes having 4 to 8 carbon atoms and aromatic hydrocarbons having 6 to 8 carbon atoms and mixtures thereof.

The lithium metal is used in particulate or powder form of not greater than 300 micron average particle size and preferably 10 to 300 microns. The lithium typically contains 0.4 to 0.76 weight percent sodium and is used in at least stoichiometric amounts, preferably in excess of stoichiometric of 1 to 100% and preferably 20- to 50% excess. The lithium dispersion is prepared for use by washing several times with pentane or some other hydrocarbon solvent of choice, to remove the dispersing fluid, and preferably subjected to high speed agitation at elevated temperatures to condition the lithium for the reaction.

The reaction temperature is from at least 50° C. up to just below the decomposition temperature of the product, and preferably from 50° C. up to the boiling point of the solvent with reflux temperatures being most preferred. The optimal temperature for running the reaction can be exceeded by using only a high boiling solvent such as decane (BP-174° C.). The useful temperature range for operating the process is between about 50° C. and about 160° C. Reduced or elevated temperature can be employed if desired but are not required. The reactants and the products are not highly corrosive so many materials of construction can be used for the reactor and related process equipment.

According to the process of the present invention, the precursor triorganosiloxyalkyl halide was prepared in a hydrocarbon solution from the corresponding haloalcohol, and hexamethyldisilazane. The lithium metal dispersion, when prepared in mineral oil, is washed free of mineral oil with a hydrocarbon solvent, dried in a stream of argon and transferred to the reaction vessel with the hydrocarbon solvent. The mixture of clean metal and hydrocarbon was heated to the reaction temperature and the functionalized triorganosilyloxyalkyl halide was added slowly to the heated lithium metal-hydrocarbon solvent mixture. The reaction temperature was controlled by cooling the reaction mixture. An exotherm typically developed after 5–30% of the halide was added. At the end of the halide feed, the reaction temperature rapidly declined to room temperature. The reaction mixture was stirred several hours at room temperature. At the end of the lithiation reaction, the reaction mixture was transferred to a sintered glass filter through which the solution was filtered rapidly with 3 psi ($20.68 \times 10^3$ Pa) Argon pressure. After the insolubles were removed by filtration, the filtrate was optionally concentrated. An essentially pure trimethylsilyloxyalkyllithium compound was obtained. The resultant non-turbid solution was analyzed for total base, active carbon-lithium (modified Watson-Estham titration) and inorganic halide.

The following examples further illustrate the invention.

A. PREPARATION OF HALOORGANOSILOXYALKANE MATERIALS

1. Preparation of 3-Chloro-2,2-dimethyl-1-trimethylsilyloxy-propane Lot 9103 (472-11)

A one liter, three-necked flask was fitted with a large magnetic stir bar, a reflux condenser, a teflon clad thermocouple, a 125 ml. pressure-equalizing addition funnel, and an argon inlet. This apparatus was dried in an oven overnight, assembled hot, and allowed to cool to room temperature in a stream of argon. The flask was charged with 122.60 grams (1.00 mole, 1.00 equivalent) of 3-chloro-2,2-dimethyl-1-propanol, and 250 ml. of cyclohexane. This afforded a homogenous solution. Hexamethyldisilazane, 85.54 grams (0.53 mole, 0.53 equivalent) was then added dropwise. There was an initial endotherm, then the temperature slowly elevated. Total feed time was seventy minutes. The catalyst, trimethylsilylchloride (0.5 ml.) was then added with a pipette. A white precipitate formed immediately. The reaction flask was swept with a slight positive flow of argon, above the level of the liquid. The reaction mixture was heated to reflux with a heating mantle. Ammonia fumes were detected exiting from the apparatus with pH paper before reflux was achieved. After three hours at reflux, the reaction mixture was clear and homogenous. After five and a half hours heating, the heat source was removed. After six hours, an aliquot was removed, and analyzed by Gas Chromatography (GC). The conversion to the desired product was 64.2% The reaction mixture was again heated to reflux, and held at reflux overnight. In the morning, the heat source was again removed, and the reaction was re-analyzed by GC. Very little change in composition. 3-Chloro-2,2-dimethyl-1-propanol and hexamethyldisilazane were both still present in the reaction mixture. Therefore, an additional 0.5 ml. of trimethylsilylchloride was added to the reaction flask. A white precipitate was again observed. The reaction mixture was heated to reflux for an additional six hours, then allowed to cool to room temperature. All the starting material had been consumed. The reaction mixture was transferred to a dry, 500 ml. single-necked flask. The product was purified by distillation through a six inch Vigreux column.

The desired product had a boiling point of 169.8°-175.0° C.

This afforded a clear, colorless oil, yield=183.07 grams, 94.1%.

GC analysis of this material indicated it was 98.9% desired product, 0.6% hexamethyldisilazane, and 0.5% unknowns.

2. Preparation of 3-Chloro-1-trimethylsilyloxy-propane Lot 8853 (461-6)

A one liter, three-necked flask was fitted with a large magnetic stir bar, a reflux condenser, a teflon clad thermocouple, a 250 ml. pressure-equalizing addition funnel, and an argon inlet. This apparatus was dried in an oven overnight, assembled hot, and allowed to cool to room temperature in a stream of argon. The flask was charged with 189.08 grams (2.00 mole, 1.00 equivalent) of 3-chloro-1-propanol, and 400 ml. of cyclohexane. This formed a two-phase solution. Hexamethyldisilazane, 167.86 grams (1.04 mole, 0.52 equivalent) was then added dropwise. There was an initial exotherm, then the temperature slowly declined. The reaction flask was swept with a slight positive flow of argon, above the level of the liquid. After about one third of the feed had been added, ammonia fumes were detected exiting from the apparatus with pH paper. Total feed time was ninety five minutes. At the end of the feed, the reaction mixture was homogenous. The reaction mixture was stirred at room temperature for two hours, then an aliquot was withdrawn, and analyzed by Gas Chromatography (GC). The conversion to the desired product was 74.6%. The catalyst, trimethylsilylchloride (0.5 ml.) was then added with a pipette. A white precipitate formed immediately. The reaction mixture was heated to reflux with a heating mantle. After two and three quarter hours heating, the heat source was removed. After six and a quarter hours, an aliquot was removed, and analyzed by GC. The conversion to the desired product was 92.0%. The reaction mixture was again heated to reflux, and held at reflux for an additional five hours, then allowed to stir at room temperature overnight. In the morning, the reaction mixture was still hazy. The conversion was 98.4%. The reaction mixture was heated to reflux for an additional three hours, then allowed to cool to room temperature. The reaction mixture was clear and homogenous at this time. The conversion was 98.8%. The total time the reaction mixture was at reflux was ten and three-quarters of an hour. The reaction mixture was transferred to a dry, one liter, single-necked flask. The product was purified by distillation through a twelve inch Vigreux column.

The desired product had a boiling point of 154°-157° C.

This afforded a clear, colorless oil, yield=298.59 grams, 90.2%.

GC analysis of this material indicated it was 97.4% desired product, 1.1% hexamethyldisilazane, 0.6% cyclohexane and 0.9% unknowns.

3. Preparation of 1-Chloro-6-trimethylsilyloxy-hexane Lot 9186 (470-33)

A one liter, three-necked flask was fitted with a large magnetic stir bar, a reflux condenser, a teflon clad thermocouple, a 125 ml. pressure-equalizing addition funnel, and an argon inlet. This apparatus was dried in an oven overnight, assembled hot, and allowed to cool to room temperature in a stream of argon. The flask was charged with 136.62 grams (1.00 mole, 1.00 equivalent) of 6-chloro-1-hexanol, and 250 ml. of cyclohexane. This afforded a homogenous solution. Hexamethyldisilazane, 85.54 grams (0.53 mole, 0.53 equivalent) was then added dropwise. There was an initial endotherm, then the temperature slowly elevated. Total feed time was sixty five minutes. The catalyst, trimethylsilylchloride (0.5 ml.) was then added with a pipette. A white precipitate formed immediately. The reaction flask was swept with a slight positive flow of argon, above the level of the liquid. The reaction mixture was heated to reflux with a heating mantle. After three and a half hours at reflux, the reaction mixture was clear and homogenous. The reaction was monitored by Gas Chromatography (GC). The reaction mixture held at reflux overnight. In the morning, the heat source was removed, and the reaction was analyzed by GC. The desired product and the chloroalcohol starting material had the same retention time. However, GC/MS analysis indicated that all the starting material had been consumed. The reaction mixture was transferred to a dry, 500 ml. single-necked flask. The solvent and low-boiling components were removed on a rotary evaporator, with a water bath temperature of 30° C. The product was purified by vacuum distillation through a six inch Vigreux column.

The desired product had a boiling point of 93.9°–97.9° C., at 10 mm Hg.

This afforded a clear, colorless oil, yield=198.58 grams, 95.1%.

GC analysis of this material indicated it was 0.02% cyclohexane, 98.69% desired product, .08% hexamethyldisilazane, and 1.21% unknowns.

B. PREPARATION OF TRIMETHYLSILOXYALKYLLITHIUM COMPOUNDS

1. Preparation of 2,2-Dimethyl-3-trimethylsilyloxy-1-propyllithium Lot 9121 (472-22)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 5.40 grams (0.778 mole, 3.00 equivalents), containing 0.43% by weight sodium, was transferred to the reaction flask with 250 ml. cyclohexane. This slurry was stirred at 450 RPMs, and heated to 62° C. with a heating mantle. The heat source was removed. 3-Chloro-2,2-dimethyl-1-trimethylsilyloxy-propane, 50.47 grams (Lot 9103, 0.259 mole, 1.00 equivalent) was then added dropwise to the reaction mixture. An exotherm was noted after 12.7% of the feed had been added. A dry ice/hexane cooling bath was employed to maintain the reaction temperature at 60°–65° C. The total halide feed time was seventy-seven minutes. The reaction temperature rapidly fell off at the end of the halide feed. The reaction mixture was stirred at room temperature for ninety minutes, then transferred to a small, sintered glass filter. The product filtered rapidly with 2 psi argon. The muds were reslurried with cyclohexane (2×50 ml.). This afforded a pale yellow solution, yield=390 ml., 297.07 grams.

Total base=13.7 wt. %.
Active C—Li=13.7 wt. %.
Soluble chloride=67 ppm.
Yield based on active C—Li=94.6%.

2. Preparation of 2,2-Dimethyl-3-trimethylsilyloxy-1-propyllithium Lot 9115 (472-17)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 5.20 grams (0.749 mole, 3.00 equivalents), containing 0.43% by weight sodium, was transferred to the reaction flask with 250 ml. cyclohexane. This slurry was stirred at 450 RPMs, and heated to 42° C. with a heating mantle. The heat source was removed. 3-Chloro-2,2-dimethyl-1-trimethylsilyloxy-propane, 50.47 grams (Lot 9092, 0.250 mole, 1.00 equivalent, 98.8% assay material) was then added dropwise to the reaction mixture. The feed was halted after 22.4% of the feed had been added. An exotherm was noted after an additional three minutes stirring. A dry ice/hexane cooling bath was employed to maintain the reaction temperature at 60°–65° C. The feed was resumed after the exotherm had subsided. The total halide feed time was eighty-nine minutes. The reaction temperature rapidly fell off at the end of the halide feed. The reaction mixture was stirred at room temperature for ninety minutes, then transferred to a small, sintered glass filter. The product filtered rapidly with 2 psi argon. The muds were reslurried with cyclohexane (2×50 ml.). This afforded a pale yellow solution, yield=420 ml., 313.19 grams.

Total base=12.8 wt. %.
Active C—Li=12.0 wt. %.
Soluble chloride=57 ppm.
Yield based on active C—Li=90.5%.

3. Preparation of 3-Trimethylsilyloxy-1-propyllithium Lot 9175 (472-38)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 6.80 grams (0.980 mole, 2.80 equivalents),containing 0.43% by weight sodium, was transferred to the reaction flask with 280 ml. cyclohexane. This slurry was stirred at 450 RPMs, and heated to 64° C. with a heating mantle. The heat source was removed. 3-Chloro-1-trimethylsilyloxy-propane, 58.29 grams (Lot 8853, 0.350 mole, 1.00 equivalent, 97.4% assay material) was then added dropwise to the reaction mixture. An exotherm was noted after 8.6% of the feed had been added. A dry ice/hexane cooling bath was employed to maintain the reaction temperature at 60°–65° C. The total halide feed time was eighty-three minutes. The reaction temperature rapidly fell off at the end of the halide feed. The reaction mixture was stirred at room temperature for sixty minutes, then transferred to a small, sintered glass filter. The product filtered rapidly with 2 psi argon. The muds were reslurried with cyclohexane (2×60 ml.). This afforded an almost colorless solution, yield=415 ml., 332.52 grams.

Total base=12.7 wt. %.
Active C—Li=1.3 wt. %.
Soluble chloride=1710 ppm.
Yield based on active C—Li=9.0 %.

4. Preparation of 6-Trimethylsilyloxy-1-hexyllithium Lot 9197 (472-45)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 5.30 grams (0.764 mole, 2.80 equivalents) was transferred to the reaction flask with 280 ml. cyclohexane. This slurry was stirred at 450 RPMs, and heated to 81° C. with a heating mantle. The heat source was removed. 6-Chloro-1-trimethylsilyloxy-hexane, 56.90 grams (Lot 9186, 0.273 mole, 1.00 equivalent) was then added dropwise to the reaction mixture. An exotherm was noted after 4.5% of the feed had been added. A dry ice/hexane cooling bath was employed to maintain the reaction temperature at 60°-65° C. The total halide feed time was sixty-nine minutes. The reaction temperature rapidly fell off at the end of the halide feed. The reaction mixture was stirred at room temperature for ninety minutes, then transferred to a small, sintered glass filter. The product filtered moderately with 3 psi argon. The muds were reslurried with cyclohexane (2×60 ml.). This afforded an almost colorless solution, yield=440 ml.,353.16 grams.

Total base=12,4 wt. %.
Active C—Li=0.5 wt. %.
Soluble chloride=1820 ppm.
Yield based on active C—Li=3.6%.

C. COMPARATIVE EXAMPLES, PRECURSOR PREPARED FROM TRIMETHYLCHLOROSILANE

1. Preparation of 2,2-Dimethyl-3-trimethylsilyloxy-1-propyllithium, Chain Extended with Two Moles of Isoprene Lot 9074 (461-97)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 5.80 grams (0.836 mole, 3.00 equivalents), containing 0.43% by weight sodium, was transferred to the reaction flask with 275 ml. cyclohexane. This slurry was stirred at 450 RPMs, and heated to 68° C. with a heating mantle. The heat source was removed. 3-Chloro-2,2-dimethyl-1-trimethylsilyloxy-propane, 54.21 grams (Lot 9043, 0.279 mole, 1.00 equivalent, 98.9% assay material) was then added dropwise to the reaction mixture. No exotherm was detected after 27.7% of the feed had been added. The feed was halted, and the reaction mixture was stirred at temperature. After an additional thirty five minutes of stirring, 2 ml. of n-butyl chloride was added to the reaction mixture with a syringe. An immediate exotherm was noted. A dry ice/hexane cooling bath was employed to maintain the reaction temperature at 60°-65° C. After the exotherm had subsided, the halide feed was resumed. The total halide feed time was one hundred and one minutes. The reaction temperature rapidly fell off at the end of the halide feed. The reaction mixture was stirred at room temperature for eighty minutes, then heated to 55° C. Isoprene, 37.95 grams (0.557 mole, 2.00 equivalents) was then added dropwise. An exotherm was noted after 18.0 % of the feed had been added. Hexane cooling was applied to maintain the reaction temperature at 60°-65° C. The total isoprene feed time was forty minutes. The reaction mixture was stirred at room temperature for sixty minutes, then transferred to a small, sintered glass filter. The product filtered rapidly with 2 psi argon. The muds were reslurried with cyclohexane (2×50 ml.). This afforded a pale yellow solution, yield=440 ml., 355.85 grams.

Total base=22.2 wt. %.
Active C—Li=19.6 wt. %.
Yield based on active C—Li=82.7%.

Preparation of 2,2-Dimethyl-3-trimethylsilyloxy-1-propyllithium Lot 9089 (472-5)

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight, assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 3.30 grams (0.479 mole, 3.28 equivalents) was transferred to the reaction flask with 150 ml. cyclohexane. This slurry was stirred at 450 RPMs, and heated to 42° C. with a heating mantle. The heat source was removed. 3-Chloro-2,2-dimethyl-1-trimethylsilyloxy-propane, 28.25 grams (Lot 9043, 0.145 mole, 1.00 equivalent, 98.8% assay material) was then added dropwise to the reaction mixture. No exotherm was detected. The feed was halted after 42.9% of the feed had been added. The reaction mixture was stirred at this temperature for three hours, but no exotherm was observed. The reaction was reheated to 40° C., and the halide feed was resumed. The reaction mixture was stirred at room temperature for seventy-five minutes, then transferred to a small, sintered glass filter. The product filtered rapidly with 2 psi argon. The muds were reslurried with cyclohexane (2×30 ml.). This afforded a colorless solution, yield=240 ml., 189.23 grams.

Total base= <0.03 wt. %.
Active C—Li= <0.21 wt. %.

The comparison examples show the improved yield and better initiation rate of the present process compared to the process of U.S. Pat. No. 5,321,148.

What is claimed is:

1. A process for producing compounds of the formula $(CH_3)_3SiORLi$ where in R is selected from alkyl groups containing 2 to 10 carbon atoms and aryl groups containing 6 to 10 carbon atoms by reacting, in an inert atmosphere, in a hydrocarbon solvent, a haloalcohol of the formula HORX wherein R is selected from alkyl groups containing 2 to 10 carbon atoms and aryl groups containing 6 to 10 carbon atoms and X is selected from chlorine or bromine, is reacted with hexamethyldisilazane at a temperature between 20° C. and the reflux temperature of the solvent after which the resulting product, a trimethylsilyloxyalkylhalide compound, is reacted at a temperature between 50° and 160° C., with powdered lithium metal to produce the $(CH_3)_3SiORLi$ compound.

2. The process of claim 1 wherein the trimethylsilyloxyalkylhalide is selected from the group consisting of 6-(trimethylsilyloxy)-1-hexylhalide, 3-(trimethylsilyloxy)-2,2-dimethyl-1-propylhalide, 3-(trimethylsilyloxy)-1-propylhalide, 4-(trimethylsilyloxy)-1-butylhalide,3-(trimethylsilyloxy)-2-methyl- 1-propylhalide and 8-(trimethylsilyloxy)-1-octylhalide.

3. The process of claim 2 wherein the halide is selected from bromine and chlorine.

4. The process of claim 1 wherein the reaction temperature is between 50° C. and 160° C.

5. The process of claim 1 wherein the lithium metal is used in an excess amount of 1 to 100% excess over the stochiometric amount.

6. The process of claim 1 wherein the fine particle size lithium metal has a particle size range of 10 to 300 microns.

7. The process of claim 6 wherein the fine particle size lithium has a sodium content of 0.40 to 0.76 weight percent.

* * * * *